(12) United States Patent
Ren et al.

(10) Patent No.: US 8,460,904 B2
(45) Date of Patent: Jun. 11, 2013

(54) METHOD OF PRODUCING REDUCED COENZYME $Q_{10}$

(75) Inventors: Lei Ren, Zhejiang (CN); Qiao Ren, Zhejiang (CN)

(73) Assignee: Zhejiang Zhongning Business Co., Ltd., Shangcheng District, Hangzhou, Zhejiang (CN)

( * ) Notice: Subject to any disclaimer, the term of this patent is extended or adjusted under 35 U.S.C. 154(b) by 348 days.

(21) Appl. No.: 13/054,560

(22) PCT Filed: Apr. 15, 2009

(86) PCT No.: PCT/CN2009/000398
§ 371 (c)(1), (2), (4) Date: Jan. 17, 2011

(87) PCT Pub. No.: WO2010/006498
PCT Pub. Date: Jan. 21, 2010

(65) Prior Publication Data
US 2011/0124062 A1    May 26, 2011

(30) Foreign Application Priority Data
Jul. 17, 2008 (CN) .......................... 2008 1 0063121

(51) Int. Cl.
*C12P 7/66* (2006.01)

(52) U.S. Cl.
USPC .......................................... 435/133

(58) Field of Classification Search
None
See application file for complete search history.

(56) References Cited

FOREIGN PATENT DOCUMENTS
WO   PCT/CN2009/000398    7/2009

*Primary Examiner* — Jon P Weber
*Assistant Examiner* — Thane Underdahl
(74) *Attorney, Agent, or Firm* — Global IP Services; Tianhua Gu

(57) ABSTRACT

The present invention relates to a method of producing high-quality reduced coenzyme $Q_{10}$ converted from oxidized coenzyme $Q_{10}$ by natural reductase. It is stable, completely natural and can be used on injection. This method is suitable for large-scale industrial production without special protective environment/atmosphere. The method of producing reduced coenzyme $Q_{10}$ includes three stages: ① phosphorylation of oxidized coenzyme $Q_{10}$ ② reduction of phosphorylated oxidized coenzyme Q $Q_{10}$ by biological reductase ③ extracting reduced coenzyme $Q_{10}$ from reductases.

10 Claims, 1 Drawing Sheet

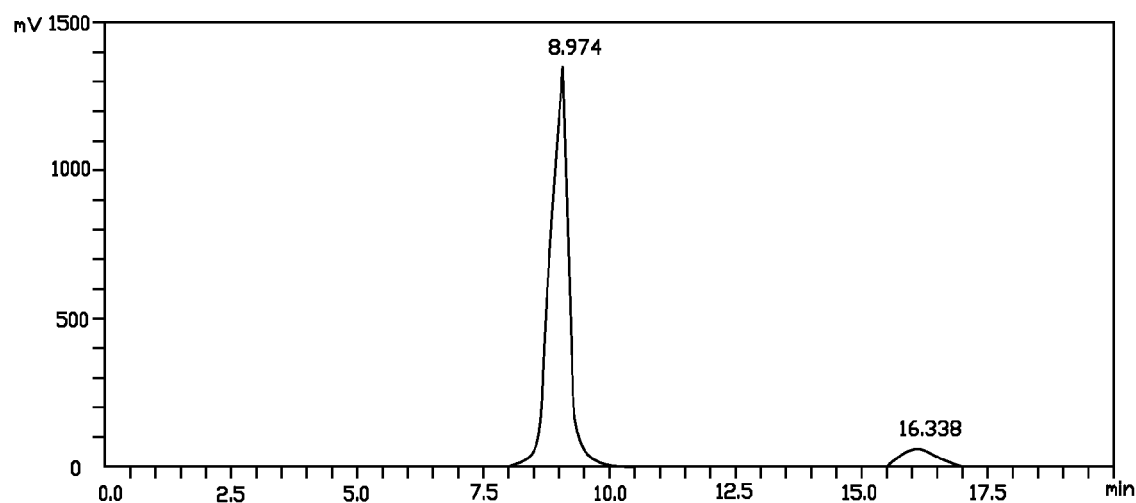

METHOD OF PRODUCING REDUCED COENZYME $Q_{10}$

CROSS REFERENCE TO RELATED PATENT APPLICATION

The present application is the US national stage of PCT/CN2009/000398 filed on Apr. 15, 2009, which claims the priority of the Chinese patent application No. 200810063121.5 filed on Jul. 17, 2008, which application is incorporated herein by reference.

FIELD OF THE INVENTION

In the present invention, it is about producing method of reduced coenzyme $Q_{10}$, especially about method of coenzyme converting to produce reduced coenzyme $Q_{10}$.

BACKGROUND OF THE INVENTION

Coenzyme $Q_{10}$, also known as ubiquinone, is an oil-soluble orange crystal at room temperature, melting point 48° C., no smell, the structure is similar to Vitamin K. Q refers to the quinone chemical group, and 10 refers to the isoprenyl chemical subunits, the structure is as following:

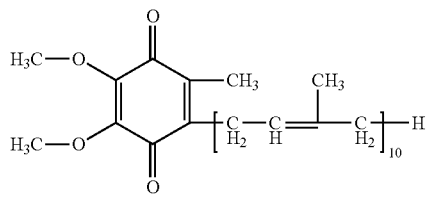

Coenzyme $Q_{10}$ has a another form of reduced Coenzyme $Q_{10}$, whose physiological functions derive from the oxidizing and reducing characteristics of benzoquinonyl and physical characteristics of isoprenoid side chain. It has two main functions on human being: first, strong effect of anti-lipid per oxidation; second, it plays an important role during the process of energy transformation from nurishments in mitochondrion. Quinone ring transfers electron and hytron in reduction breathing chain. This function is essential for lives and vital for ATP. Reduced Coenzyme Q10 is a natural cell antioxidant and metabolism activator. Meanwhile, it protects and resumes Integrality of biomembrane structure, stabilize membrane potential and improve body's non-special immunity. It is used as assistant treatment in heart and liver clinical curing.

It is Coenzyme $Q_{10}$ which has the two effects as mentioned above. Therefore, producing Coenzyme $Q_{10}$ especially natural Coenzyme $Q_{10}$ will provide a direct effect, However, Coenzyme $Q_{10}$ will easily get reduced and is difficult to achieve industrial production. Reduce Coenzyme $Q_{10}$ a white crystal two-reduction from Coenzyme $Q_{10}$. It is known reduce Coenzyme $Q_{10}$ can be obtained by using reducing agent reduction on Coenzyme $Q_{10}$, such as WO01/52822A1. There is a problem of molecule reduction on case reduce Coenzyme $Q_{10}$, which is reduced by chemical reducing agent, is used on healthy food, beverage, cosmetic and drugs. Up to now, commercial reduce Coenzyme $Q_{10}$ is not able to manufactured. Additionally, we have to solve others problems like how to protect and stabilize reduce Coenzyme $Q_{10}$.

Furthermore, those, which rise environment polluting and are uncertainly safe to human health, like chemical reducing agents, protestants and additives, organic solvents, are widely used on producing reduce Coenzyme $Q_{10}$, exists in cosmetic, food and drugs. The harm of reducing agent and protestant is even more than reduced Coenzyme $Q_{10}$'s effect.

SUMMARY OF THE INVENTION

In view of the foregoing, the present invention is targeted to offer an enzymatic conversion method of producing reduced Coenzyme Q10 which is very natural, green, safe and reliable.

The present invention contains following techniques:
(1) phosphorylation of oxidized coenzyme $Q_{10}$ (2) reduction of phosphorylated oxidized coenzyme $Q_{10}$ by biological reductase (3) extracting reduced coenzyme $Q_{10}$ from reductases. The foregoing reaction formula is as:

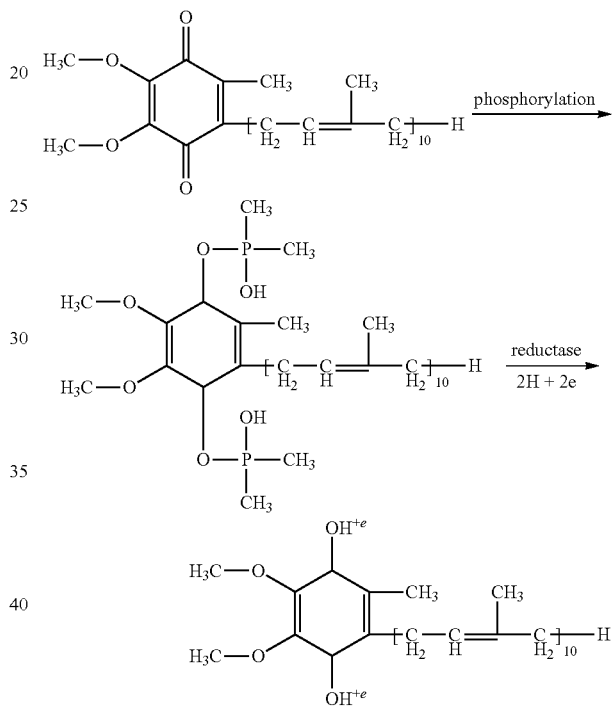

The method according to stage 2, wherein it is preferred that:
(1) Choosing bacterial, microzyme, or epiphyte which contains coenzyme $Q_{10}$ to develop.
(2) Disrupting cells, and deposit them with ammonium sulfate of 30%-70% weight percentage.
(3) Isolating the precipitate, dialysis the foregoing to get biological reduced coenzyme $Q_{10}$.

The above biological reductase and phosphorylation oxidized are of fine reduction in a higher yield.

As preferred, the microzyme or epiphyte is photosynthetic bacteria or red *Pseudomonas*.

As preferred, the cells are disrupted by Ultrasonic Cell Disruptor.

As preferred, washing precipitate in 35° C.-45° C. cold water for 1-2 hours after deposition, and centrifugating it with Cooling centrifuges for 10-30 minutes under 1° C.-3° C., 10000-15000 r/min atmosphere, then cast supernatant, adding phosphoric acid solution to dialysis.

As more preferred, Sepharos 4B is added to stir after dialysis, and washing three times with phosphoric acid solution, added with sodium hydroxide to get a pH 8.5, breakdown, freeze drying the liquid after filtering with cool drying machine to obtain foregoing coenzyme $Q_{10}$.

As preferred, the phosphorylation of oxidized coenzyme $Q_{10}$ is carried out by dissolving the oxidized coenzyme $Q_{10}$ in phosphoric acid solution, then adding phosphonolipide or any other phosphonolipide salt in an amount of 2-10% weight of oxidized coenzyme $Q_{10}$ with 10-120 minutes stirring under 28° C.-45° C. atmosphere.

As more preferred, wherein the phosphoric acid solution pH range should be adjusted to be 6.0-8.2.

As preferred, the extraction from film pressed filtering reactants is of vacuum to be concentrated from film pressed filtering with adding water during the concentration. Crystallization under 2° C.-10° C., then cooling and drying the crystalline to obtain the foregoing reduced coenzyme $Q_{10}$.

As more preferred, the film pressure of filtering is 0.1 MPa-0.8 MPa

As above motioned method of natural enzymatic conversion oxidized coenzyme $Q_{10}$, it is able to manufacture in a large-scale without special protective atmosphere. The foregoing obtained reduced coenzyme $Q_{10}$, owns the following features:
(1) Stability. No reducing by dioxygen or any chemical compound. Coenzyme $Q_{10}$ remains its qualities in phosphoric acid solution of pH6.0-8.2, and has a shelf life of over 2 years below 50° C.
(2) Full nature. It is completely safe to use on food, drug and cosmetic while no reducing agent, antioxidant or protectant are used during the process.
(3) Water-solubility. It can be used on injection which is completely water soluble after phosphorylation.

BRIEF DESCRIPTION OF THE DRAWINGS

FIG. 1 is as HPLC prints of the present invention of reduced coenzyme $Q_{10}$.

DETAIL DESCRIPTION OF THE INVENTION

Example 1

Method of using bacteria to produce biological reductase:
1. Seed selection: *Rhodobacter sphaeroides*, a healthy sporty bacteria seed of 0.5-0.9 micron width, 1.2-2.0 micron length, gammae, no capsule, single polar flagellum.
2. Preparing zymotic fluid: 5.5 g monometallic sodium orthophosphate', 1.5 g Dlmalic acid, 2.0 g sodium acetate, 2.0 g sodium hydroxide, 1.0 g ammonium chloride, 0.25 g magnesium chloride, 0.05 g calcium chloride, 3.5 g glucose dissolved in 1.0 L distilled water, stirring pH range is between 6.5-7.0.
3. Prepare 10 triangular flasks of 250 mL, pouring 100 mL inoculum into each flask after sterilization. Seal them after inoculation. Put them into incubator for 72 hours in sunlight of 32° C., and then get out.
4. Collecting inoculum, centrifugating it with centrifuge for 20 minutes, 6000 rev/min, then disrupt the mycelium after centrifugation, adding 200 ml brine of 3% weight percentage in still for 1 hour. then collect supernatant, adding 500 ml ammonium sulfate, washed by 40° C. water for 1.5 hour, next centrifugation with cooling centrifuge for 20 minutes, 12000 rev/min at 4° C. Then cast supernatant, adding 300 mL phosphoric acid solution to dialysis, stirring with 100 ml Sepharos 4B, washed three times with 200 ml phosphoric acid solution. Adding sodium hydroxide to adjust to pH8.5, break downing, cool drying the filtered liquid with cooling drying machine to obtain 80 mg biological reductase.

Example 2

Method of using microzyme to produce biological reductase:
1. Seed selection: Schizosaccharomyces Promb.
2. Preparing zymotic fluid: beef extract 0.3 g, peptone 1.0 g, Nacl 0.5 g, water 100 mL, adjust Ph to 7.0-7.2, adding water into breaker, weigh up beef extract, peptone and Nacl, warm them up to be melted, adjust the pH to 7.0~7.2, packing each with cotton tampon, then high pressure steaming sterilizing to finish.
3. Preparing 10 triangular flasks of 250 mL, pouring 100 mL inoculum into each flask after sterilization. Seal them after inoculation. Put them into incubator for 72 hours in sunlight of 35° C., and then get out.
4. Collecting inoculum, centrifugating it with centrifuge for 20 minutes, 6000 rev/min, then disrupt the mycelium after centrifugation, adding 200 ml brine of 3% weight percentage in still for 1 hour, then collect supernatant, adding 500 ml ammonium sulfate, washed by 40° C. water for 1.5 hour, next centrifugating with cooling centrifuge for 20 minutes, 12000 rev/min at 5° C. Then cast supernatant, adding 300 mL phosphoric acid solution to dialysis, stirring with 100 ml Sepharos 4B, washed three times with 200 ml phosphoric acid solution. Adding sodium hydroxide to adjust to pH8.5, break downing, cool drying the filtered liquid with cooling drying machine to obtain 80 mg biological reductase.

Example 3

Method of using fungus to produce biological reductase:
1. Seed selection: Entophytic
2. Preparing zymotic fluid: beef extract 0.3 g, peptone 1.0 g, Nacl 0.5 g, agar 1.5 g, water 100 mL.
3. Preparing 10 triangular flasks of 250 mL, pouring 100 mL inoculum into each flask after sterilization. Seal them after inoculation Put them into incubator for 72 hours in sunlight of 36° C., and then get out.
4. Collecting inoculum, centrifugating it with centrifuge for 20 minutes, 6000 rev/min, then disrupt the mycelium after centrifugation, adding 200 ml brine of 3% weight percentage in still for 1 hour. then collect supernatant, adding 500 ml ammonium sulfate, washed by 40° C. water for 1.5 hour, next centrifugating with cooling centrifuge for 20 minutes, 12000 rev/min at 2° C. Then cast supernatant, adding 300 mL phosphoric acid solution to dialysis, stirring with 100 ml Sepharos 4B, washed three times with 200 ml phosphoric acid solution. Adding sodium hydroxide to adjust to pH8.5, break downing, cool drying the filtered liquid with cooling drying machine to obtain 80 mg biological reductase.

Example 4

Using oxidized coenzyme $Q_{10}$ to react with reductase, converting into natural reduced coenzyme $Q_{10}$.
1. phosphorylating the oxidized coenzyme $Q_{10}$, then dissolve 250 g oxidized coenzyme $Q_{10}$ in 1000 mL phosphoric acid solution ((pH7.4), then adding 12.5 g phosphonolipide in an amount of 5% weight of oxidized coenzyme $Q_{10}$ with 10-120 minutes stirring under 37° C. atmosphere.
2. Prepare biological reductase according to example 1-3.

3. Put the phosphorylated oxidized into reactor, adding 80 g biological reductase, stirring for 10-30 minutes at 37° C.-60° C. atmosphere
4. Film filtering: with a pressure of 0.5 mPa, making filtering at 30° C., and leave the filtrate in the air for above 5 hours at 2° C.
5. Concentrating the filtrate at 35° C., 200 Pa vacuum atmosphere.
6. Washing the concentration for 3 times with water, and then crystallizing at 2° C.
7. Obtaining 248.2 g crystal in the cooling drying machine, the purity reaches 99.4%. As tested, no oxidized coenzyme $Q_{10}$ exists.

Testing Example

Prepare reduced coenzyme $Q_{10}$ according to example 4, test it with HPLC.
Equipments: Shimazu wave length: 275 nm
Mobile phase: enthanol:methanol=1:1 (v:V)
Column: octadecyl silica gel column; length: 180 mm inner diameter: 3.2 mm
Weigh up reduced coenzyme $Q_{10}$
20 mg, dissolved in enthaol to 100 ml, sample size 20 ul, using three-point external standard method to calculate assay.
Appearance time 8.974 min. Tested chart as Chart 1.

What is claimed is:

1. A method of producing reduced coenzyme $Q_{10}$ comprising the following steps:
   (1) phosphorylation of oxidized coenzyme $Q_{10}$;
   (2) reduction phosphorylated oxidized coenzyme $Q_{10}$ by biological reductases;
   (3) extracting reduced coenzyme from reductases.
2. The method according to claim 1, wherein the biological reductases are made by:
   (1) choosing bacteria, microzyme or epiphyte containing coenzyme $Q_{10}$ and cultivating the bacteria, microzyme or epiphyte containing coenzyme $Q_{10}$;
   (2) disrupting cells cultivated from step (1), and deposit them with ammonium sulfate in a concentration of 30%-70% weight percentage to get a precipitate;
   (3) isolating the precipitate gotten from (2) by using dialysis; then
   (4) use the isolated precipitate of (3) to reduce coenzyme $Q_{10}$.
3. The method according to claim 2, wherein the bacteria, microzyme or epiphyte is photosynthetic bacteria or red pseudomonas.
4. The method according to claim 2, wherein the cells are disrupted by an ultrasonic cell disruptor.
5. The method according to claim 2, 3 or 4 wherein:
   (1) wash the precipitate in 35° C.-45° C. cold water for 1-2 hours after the depositing, then;
   (2) centrifugate the precipitate while cooling the centrifuge for 10-30 minutes under 1° C.-3° C. atmosphere, at 10000-15000 rev/min, then isolate supernatant;
   (3) add phosphoric acid solution to the supernatant.
6. The method according to claim 5, wherein Sepharose 4B is added to stir after dialysis, then wash three times with phosphoric acid solution, add sodium hydroxide to get a pH 8.5, then freeze dry the liquid after filtering to obtain coenzyme $Q_{10}$.
7. The method according to claim 1 or 2, wherein the phosphorylation of oxidized coenzyme $Q_{10}$ comprises the following steps:
   (1) dissolve the oxidized coenzyme $Q_{10}$ in phosphoric acid solution, then;
   (2) adding phosphonolipid or phosphonolipid salt in an amount of 2-10% weight of the oxidized coenzyme $Q_{10}$ with 10-120 minutes stirring under 28° C.-45° C. atmosphere.
8. The method according to claim 7, wherein the phosphoric acid solution has a pH of 6.0-8.2.
9. The method according to claim 1 or 2, wherein the extraction comprises the following steps:
   (1) filter the reactants under vacuum pressure into a film while adding water and collecting the filtrate;
   (2) vacuum concentrate the filtrate;
   (3) crystallize the filtrate by cooling to 2° C.-10° C.; then
   (4) drying the crystals to obtain the reduced coenzyme $Q_{10}$.
10. The method according to claim 9, wherein the pressure of filtering is 0.1 MPa-0.8 MPa.

* * * * *